| United States Patent [19] | [11] | 4,171,376 |
|---|---|---|
| Collins, et al. | [45] | Oct. 16, 1979 |

[54] ARYLOXYALKYL KETO-ESTERS

[75] Inventors: Joseph C. Collins, East Greenbush; Guy D. Diana, Stephentown, both of N.Y.

[73] Assignee: Sterling Drug Inc., New York, N.Y.

[21] Appl. No.: 913,454

[22] Filed: Jun. 7, 1978

Related U.S. Application Data

[60] Division of Ser. No. 725,160, Sep. 21, 1976, Pat. No. 4,133,959, which is a continuation-in-part of Ser. No. 576,311, May 12, 1975, Pat. No. 4,031,246, which is a continuation-in-part of Ser. No. 381,406, Jul. 23, 1973, Pat. No. 3,933,837.

[51] Int. Cl.$^2$ .................... A01N 9/24; A61K 31/235; C09F 5/00
[52] U.S. Cl. .................................. 424/308; 260/405; 260/408; 260/410; 424/305
[58] Field of Search ................... 260/405, 408, 410 R; 424/308, 305

[56] References Cited

U.S. PATENT DOCUMENTS

| 3,686,222 | 8/1972 | Chodnekar | 260/340.5 |
|---|---|---|---|
| 3,787,443 | 1/1974 | Erickson | 260/327 E |
| 3,829,475 | 8/1974 | Collins | 260/520 |
| 3,933,837 | 1/1976 | Collins et al. | 260/340.5 |

*Primary Examiner*—John Niebling
*Attorney, Agent, or Firm*—Thomas L. Johnson; B. Woodrow Wyatt

[57] ABSTRACT

Aryloxyalkyl keto-esters, useful as anti-viral agents, are prepared from an aryloxyalkyl halide and an alkali metal enolate salt of a keto-ester.

9 Claims, No Drawings

ARYLOXYALKYL KETO-ESTERS

This application is a divisional of copending application Ser. No. 725,160, filed Sept. 21, 1976, now U.S. Pat. No. 4,133,959, which is in turn a continuation-in-part of copending application Serial No. 576,311 filed May 12, 1975, now U.S. Pat. No. 4,031,246, which is in turn a continuation-in-part of application Ser. No. 381,406, filed July 23, 1973, now U.S. Pat. No. 3,933,837.

BACKGROUND OF THE INVENTION (a) Field of the Invention

This invention relates to aryloxyalkyl diketone and keto-esters, to the preparation thereof and to compositions and methods for the use thereof as anti-viral agents.

(b) Description of the Prior Art

Chodnekar et al. U.S. Patent 3,686,222 discloses ethers of the formula R-O-Ar wherein Ar is methylenedioxyphenyl and R is an aliphatic hydrocarbon radical or an epoxide derivative thereof, useful as pesticides having juvenile hormone activity.

Erickson U.S. Pat. No. 3,787,443 discloses ethers of the formula R-O-Ar wherein Ar is methylenedioxyphenyl or other substituted phenyl groups, and R is an aliphatic hydrocarbon radical or an epoxide or episulfide derivative thereof, useful as pesticides having juvenile hormone activity.

Collins U.S. Pat. No. 3,829,475 discloses diketones and keto-esters of the formula RR'CH-Alk-Ar wherein R is acyl, R' is acyl or carboalkoxy, Alk is an alkylene bridge and Ar is phenyl or substituted phenyl, useful as pesticidal and antiviral agents; no aryl ethers are disclosed.

SUMMARY OF THE INVENTION

In a composition of matter aspect, the invention relates to compounds of the formula RR'CH-Alk-O-Ar wherein R is alkanoyl or carbalkoxy, R' is alkanoyl, Alk is alkylene and Ar is phenyl or substituted phenyl, useful as anti-viral agents.

In further composition of matter aspects, the invention relates to intermediates of the formula RR'CH-Alk-X where Alk is alkylene and X is Br or I; and intermediates of the formula 2-Cl-4-CH$_3$O-C$_6$H$_3$-O-Alk'-Cl where Alk' is alkylene interrupted by an oxygen atom.

In a further composition of matter aspect, the invention relates to a composition for combatting viruses which comprises an antivirally effective amount of a compound of the formula RR'CH-Alk-O-Ar in admixture with a suitable carrier or diluent.

In a process aspect, the invention relates to a process for obtaining the compounds of the invention by treating a compound of the formula X-Alk-O-Ar, where X is bromine or iodine, with a compound of the formula RR'CH-M+ where M+ is an alkali metal cation; or, conversely, reacting a compound of the formula RR'CH-Alk-X with a compound of the formula ArO-M+.

In a further process aspect, the invention relates to a method for combatting viruses which comprises contacting the locus of said viruses with an anti-virally effective amount of a compound of the formula RR'CH-Alk-OAr in admixture with a suitable carrier or diluent.

DETAILED DESCRIPTION INCLUSIVE OF PREFERRED EMBODIMENTS

The compounds of the invention are of the structural formula

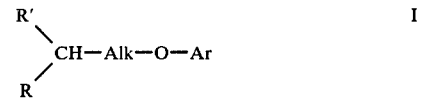

wherein:
- Alk is alkylene of 3 to 10 carbon atoms optionally interrupted by an oxygen atom separated by at least two carbon atoms from the terminal bonds of Alk;
- R is alkanoyl of 2 to 6 carbon atoms;
- R' is alkanoyl of 2 to 6 carbon atoms or carboalkoxy of 2 to 6 carbon atoms;
- and Ar is phenyl or phenyl substituted by one to three substituents selected from the group consisting of alkyl of 1 to 4 carbon atoms, alkoxy of 1 to 4 carbon atoms, alkylthio of 1 to 4 carbon atoms, alkoxyalkoxy of 3 to 6 carbon atoms, hydroxyalkoxy of 2 to 4 carbon atoms, halogen, cyano, nitro, acetyl, sulfo, aminosulfonyl, trifluoromethyl, trifluoromethoxy, hydroxy, benzyloxy, carboxy, carboalkoxy of 2 to 4 carbon atoms, acyloxy of 1 to 10 carbon atoms, dialkylamino where alkyl has from 1 to 4 carbon atoms, and dialkylaminoalkoxy where alkyl has from 1 to 4 carbon atoms and alkoxy has from 2 to 4 carbon atoms.

Also within the scope of the invention are pharmaceutically acceptable heavy metal chelates of the foregoing compounds, wherein the metal is complexed with the carbonyl groups of the diketone or keto-ester moiety. Such metals include copper (valence II), nickel, cobalt and the like.

In the above general formula I, Alk stands for a saturated aliphatic hydrocarbon bridge containing from 3 to 10 carbon atoms. The alkylene bridge may be straight or branched. A preferred class of compounds are those where Alk is straight chain alkylene of 3 to 10 carbon atoms, and if the Alk bridge is branched, it is preferred that it be symmetrical, that is with the branching at the same relative positions from either end of the bridge.

The alkylene bridge, Alk, is optionally interrupted by an oxygen atom separated by at least two carbon atoms from the terminal bonds of Alk. The oxygen atom is preferably in the center of the alkylene bridge, equidistant from the terminal bonds of Alk.

The carbon chains of R and R' can be straight or branched.

When two or three monovalent substituents are present on the phenyl ring of Ar, they can be the same or different. In the event alkoxyalkoxy is present on the phenyl ring, it is preferred that the two oxygen atoms therein be separated by at least two carbon atoms. It is also preferred that no more than one nitro or sulfo group be present on the phenyl ring.

The compounds of the invention are prepared according to the following reaction sequence:

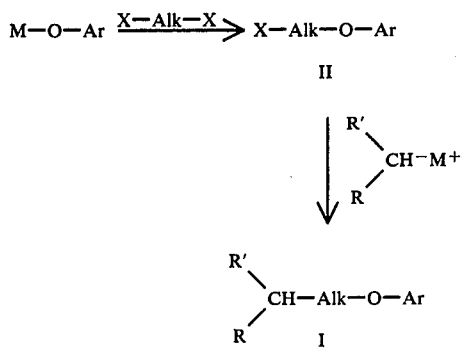

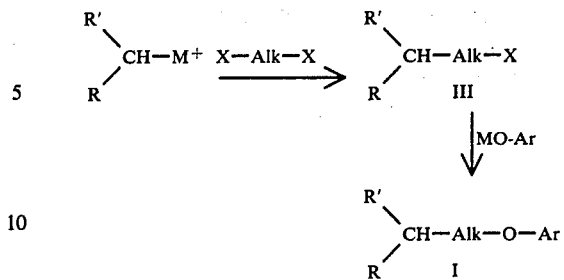

An alkali metal salt of a phenol (HOAr), M-O-Ar, where M is alkali metal, preferably sodium or potassium, is interacted with an alkylene dihalide, X-Alk-X, where X is chlorine, bromine or iodine. The reaction takes place with moderate heating, between about 50° and 100° C. in an inert solvent using equimolar quantities of reactants, or preferably a stoichiometric excess of dihalide to minimize di-ether (Ar-O-Alk-O-Ar) formation. The di-ether that is formed is readily separated from the desired mono-ether (II), because the former is a relatively high melting solid which separates readily from organic solvents while the mono-ether remains in solution.

In the final step, the mono-ether, X-Alk-O-Ar (II), is treated with the alkali metal enolate salt of a diketone or keto-ester of formula RR′CH—M+, where R and R′ have the meanings given hereinabove and M+ is an alkali metal cation, preferably lithium, sodium or potassium. The reaction takes place in an inert solvent under anhydrous conditions at ambient temperature or slightly above (25°–70° C.). If the mono-ether, X-Alk-O-Ar, is a chloride (X=Cl), it is preferably converted to the more reactive iodide (x=I) with an alkali metal iodide, prior to the final alkylation step.

If it is desired to obtain compounds of formula I wherein Ar is substituted by one to three hydroxy groups, the reaction between M-OAr and X-Alk-X can be carried out with the corresponding compounds where Ar is substituted by one to three benzyloxy or acyloxy groups. The benzyloxy or acyloxy group or groups can then be cleaved by catalytic hydrogenolysis or hydrolysis, respectively.

It is not, however, essential that phenolic hydroxy groups be protected in the form of ethers or esters at the final stage of the synthesis because the diketone or keto-ester reactant, RR′CH₂, is more acidic than the phenolic hydroxyl; hence the desired alkylation with the iodides or bromides (II, X is I or Br) will take place without affecting any phenolic hydroxy groups which may be present.

Alternatively, in the final step, the alkali metal enolate salt can be replaced by a heavy metal chelate of the diketone or keto-ester. Appropriate heavy metal chelates include the copper, nickel and cobalt chelates.

An alternative approach to the compounds of the invention is depicted in the following reaction sequence:

In this alternative approach an alkali metal enolate salt or a heavy metal chelate of a diketone or keto-ester (RR′CH₂) is interacted with an alkylene dihalide, X-Alk-X. The reaction takes place in an inert solvent under anhydrous conditions at ambient temperature or slightly above (20°–70° C.), using equimolar quantities of reactants or a stoichiometric excess of dihalide. The resulting haloalkyl diketone or keto-ester of formula III is then interacted with an alkali metal salt of a phenol (HOAr), which reaction takes place with moderate heating, between about 50° and 100° C. in an inert solvent under anhydrous conditions. In this approach, any free hydroxy groups present in Ar should be protected in the form of the benzyl ether or an ester in order to prevent competing reactions with the haloalkyl diketone.

The intermediates of formula III are novel compounds and within the purview of the invention.

It is preferred to carry out the initial etherification step with a dibromide (X-Alk-X where X is Br) because of the more ready availability of dibromides as compared to diiodides. The resulting bromide (X-Alk-O-Ar or RR′CH-Alk-X where X is Br) can be interacted directly with the alkali metal enolate salt RR′CH—M+ or phenolate ArO—M+, respectively; or if desired converted to the corresponding iodide (X-Alk-O-Ar or RR′CH-Alk-X where X is I) which reacts somewhat more easily with the enolate or phenolate salt than does the bromide. The conversion of II (X=Br) to II (X=I) or III (X=Br) to III (X=I) is effected by heating the former with sodium or potassium iodide in an inert solvent, e.g. acetone.

The dihalides, X-Alk-X, where Alk is branched or oxygen interrupted are preferably symmetrical, that is, the branching or hetero atom is in the same relative position or positions with respect to the terminal halogen atoms, in order to avoid production of mixtures upon ether formation.

It is also possible to employ chlorobromoalkanes as the dihalide reactant, namely, Cl-Alk-Br. The use of such mixed dihalides has the advantage that di-ether formation is eliminated or minimized, since reaction occurs preferentially with the bromine atom, especially if stoichiometric proportions of phenol and dihalide are used. Furthermore, it is possible by this variation in the procedure to obtain compounds with unsymmetrically branched or oxygen interrupted alkylene bridges without producing mixtures. The resulting chloroalkoxy aryl ether, Cl-Alk-O-Ar, or chloroalkyl diketone or keto-ester, Cl-Alk-CHR′R, must then be converted to the corresponding bromo or iodo compound before it will react with the alkali metal phenolate or the alkali metal enolate salt of a diketone or keto-ester, respectively. The chlorobromoalkane starting materials can be prepared by reduction, e.g. with lithium aluminum hydride, of a chloro-ester, Cl-Alk'-COOCH₃, to afford a chloroalkanol, Cl-Alk-OH, followed by replacement of the hydroxy group with bromine, e.g. with phosphorus tribromide.

It is preferred to prepare compounds of formula I where the aryl group is substituted by acyloxy by esterification of the corresponding hydroxy compounds with the appropriate acid halide or acid anhydride. The acyloxy groups are derived from carboxylic acids having from one to about ten carbon atoms, and having a molecular weight less than about 200. Representative of the acyl radicals which can be present are lower-alkanoyl radicals, e.g., formly, acetyl, propionyl, butyryl, isobutyryl, caproyl, heptanoyl, octanoyl, trimethylacetyl, and the like; carboxy-lower-alkanoyl radicals, e.g., succinyl (β-carboxypropionyl); cycloalkyl-lower-alkanoyl radicals, e.g., β-cyclopentylpropionyl, β-cyclohexylpropionyl, and the like; monocarbocyclic aroyl radicals, e.g., benzoyl, p-toluyl, p-nitrobenzoyl, 3,4,5-trimethoxybenzoyl, and the like; monocarbocyclic aryl-lower-alkanoyl or alkenoyl radicals, such as phenylacetyl, β-phenylpropionyl, cinnamoyl, and the like; and monocarbocyclic aryloxy-lower-alkanoyl radicals, such as p-chlorophenoxyacetyl, and the like; and amino-lower-alkanoyl, such as glycinyl, alaninyl, diethylaminopropionyl, piperidinopropionyl, pyrrolidinopropionyl, morpholinobutyryl, and the like. When monocarbocyclic aryl groups are present in the ester moieties, monocarbocyclic aryl includes phenyl and phenyl substituted by from one to three lower-alkyl, lower-alkoxy, halogen or nitro groups, which substituents, if plural, can be the same or different. It is preferred that no more than one nitro group be present.

It is preferred to prepare compounds of formula I where the aryl group is substituted by carboxyl (COOH) by hydrolysis of the corresponding compounds of formula I where the aryl group is substituted by carboalkoxy. A sulfo group can be introduced into the aryl group of a compound of formula I by direct sulfonation with sulfuric acid.

It is preferred to prepare compounds of formula I where the aryl group is substituted by dialkylaminoalkoxy by etherification of the corresponding compounds of formula I where the aryl group is substituted by hydroxy, effected by reacting an alkali metal salt of the latter with a dialkylaminoalkyl halide.

Biological evaluation of the compounds of the invention has shown that they possess antiviral activity. They have been found to be effective against one or more of a large variety of RNA and DNA viruses, including Myxoviruses, e.g. influenza types A₀, A₁, A-2, B; Paramyxoviruses, e.g. parainfluenza types 1, 2, 3, and mumps virus; Picornaviruses, e.g. human rhinoviruses, Coxsackie viruses types A, B, ECHO viruses, equine rhinoviruses; Reoviruses, types 1, 2, 3; Arboviruses, e.g. equine encephalomyelitis (Eastern, Western and Venezuelan), Semliki Forest virus; miscellaneous RNA viruses, e.g. measles, distemper, respiratory syncytial, rubella, vesicular stomatitis, hepatitis; Herpes viruses, e.g. HSV type I, II, herpesvirus simiae, herpesvirus varicellae, infectious bovine rhinotracheitis, cytomegalovirus, Marek's disease virus, Epstein-Barr virus; Poxviruses, e.g. variola, vaccinia; leukemogenic viruses. Both in vitro and in vivo antiviral activity have been found in the compounds of the invention. The in vitro testing of the compounds showed that they had minimal growth inhibitory concentrations (mic) ranging from about 0.3 to about 50 micrograms per milliliter. The mic values were determined by standard serial dilution procedures.

The structures of the compounds of the invention were established by the modes of synthesis, by elementary analysis, and by infrared and nuclear magnetic resonance spectral determinations.

A still further aspect of the invention relates to compositions for combatting viruses which comprise an antivirally effective amount of at least one compound of formula I in admixture with a suitable carrier or diluent, and to the method of combatting viruses by contacting the locus of said viruses with said compositions.

The Antiviral compositions are formulated by preparing a dilute solution or suspension in an organic or aqueous-organic medium, for example ethyl alcohol, acetone, dimethylsulfoxide, and the like; and are applied to the locus to be disinfected by conventional means such as spraying, swabbing or immersing. Alternatively, the compounds can be formulated as ointments or creams by incorporating them in conventional ointment or cream bases, such as alkylpolyether alcohols, cetyl alcohol, stearyl alcohol and the like; as jellies by incorporating them in conventional jelly bases such as glycerin and tragacanth; or as aerosol sprays or foams.

The following examples will further illustrate the invention.

EXAMPLE 1

(a) 7-(2-Chloro-4-methoxyphenoxy)heptyl bromide.

A solution of 6.9 g. (0.172 mole) sodium hydroxide pellets in 160 ml. absolute ethanol was prepared with stirring at room temperature and a solution of 25 g. (0.158 mole) 2-chloro-4-methoxyphenol in 25 ml. absolute ethanol was added in a fine stream. The solution was stirred at room temperature for 15 minutes, then warmed gently in a steam bath (40°-45° C.) for one-half hour. The reaction mixture was chilled to about 5° C. in an ice bath and 123 g. (0.477 mole) 1,7-dibromoheptane was added dropwise over a 30 minute period. The reaction mixture was stirred and allowed to warm to room temperature, then stirred for 6 hours at room temperature and boiled at reflux for fifteen hours.

The reaction mixture was evaporated in vacuo and the residue taken up in ether, washed well with water and evaporated. Unreacted 1,7-dibromoheptane was collected by distilling the residue at 10 mm. to pot temperature 160°-170° C. The pot residue was distilled at 110°-115° C. (0.025 mm.) to give 38.5 g. of 7-(2-chloro-4-methoxyphenoxy)heptyl bromide.

By replacing the 2-chloro-4-methoxyphenol in the foregoing preparation by a molar equivalent amount of phenol, p-chlorophenol, p-bromophenol, or 2,4,6-trichlorophenol, there can be obtained, respectively, 7-phenoxyheptyl bromide, 7-(4-chlorophenoxy)heptyl bromide, 7-(4-bromophenoxy)heptyl bromide, or 7-(2,4,6-trichlorophenoxy)heptyl bromide.

By replacing the 1,7-dibromoheptane in the foregoing preparation by a molar equivalent amount of 1,3-dibromopropane there can be obtained 3-(2-chloro-4-methoxyphenoxy)propyl bromide.

(b) 7-(2-Chloro-4-methoxyphenoxy)heptyl iodide.

A mixture of 38.5 g. (0.115 mole) of 7-(2-chloro-4-methoxyphenoxy)heptyl bromide and 17.3 g. (0.115 mole) of sodium iodide in 450 ml. of acetone was stirred at reflux for three hours. The reaction mixture was filtered hot, concentrated in vacuo, and the residue partitioned between water and ether. The ether layer was dried over anhydrous sodium sulfate and concentrated to give 44 g. of 7-(2-chloro-4-methoxyphenoxy)-heptyl iodide, used directly in the next reaction.

(c) Ethyl 2-acetyl-9-(2-chloro-4-methoxyphenoxy)nonanoate [I; Ar is 2-Cl-4-CH$_3$OC$_6$H$_3$, Alk is (Ch$_2$)$_7$, R is CH$_3$CO, R' is CH$_3$CH$_2$OCO].

Ethyl acetoacetate (11.9 g., 0.0915 mole) was added dropwise to a stirred slurry of 0.656 g. (0.0830 mole) of lithium hydride in 75 ml. of dimethylformamide. The latter mixture was stirred for one hour at 90°–95° C., and there was then added in a fine stream 14.66 g. (0.383 mole) of 7-(2-chloro-4-methoxyphenoxy)heptyl iodide in 30 ml. of dimethylformamide. The reaction mixture was heated at 60°–70° C. for 42 hours and then poured into ice and dilute hydrochloric acid. The mixture was extracted with ether and the latter washed with water and saturated sodium chloride solution, dried over anhydrous sodium sulfate and concentrated. The residue (21 g.) was distilled, b.p. 197°–202° C. (0.015 mm. ), and redistilled, b.p. 205°–206° C. (0.03 mm.) to give 4 g. of ethyl 2-acetyl-9-(2-chloro-4-methoxyphenoxy)nonanoate.

Anal. Calcd. for C$_{20}$H$_{29}$ClO$_5$: C, 62.41; H, 7.59; Cl, 9.21. Found: C, 62.12; H, 7.61; Cl, 9.29.

By replacing the ethyl acetoacetate in the foregoing preparation by a molar equivalent amount of methyl acetoacetate or pentyl 3-oxooctanoate there can be obtained, respectively, methyl 2-acetyl-9-(2-chloro-4-methoxyphenoxy)nonanoate [I; Ar is 2-Cl-4-CH$_3$OC$_6$H$_3$, Alk is (CH$_2$)$_7$, R is CH$_3$CO, R' is CH$_3$OCO], or pentyl 2-hexanoyl-9-(2-chloro-4-methoxyphenoxy)nonanoate [I; Ar is 2-Cl-4-CH$_3$OC$_6$H$_3$, Alk is (CH$_2$)$_7$, R is CH$_3$(CH$_2$)$_4$CO, R' is CH$_3$(CH$_2$)$_4$OCO].

By replacing the 7-(2-chloro-4-methoxyphenoxy)-heptyl iodide in the foregoing preparation by a molar equivalent amount of 7-phenoxyheptyl iodide, 7-(4-chlorophenoxy)heptyl iodide, 7-(4-bromophenoxy)heptyl iodide, 7-(2,4,6-trichlorophenoxy)heptyl iodide, or 3-(2-chloro-4-methoxyphenoxy)propyl iodide, prepared from the corresponding bromides as described above in part (b), there can be obtained, respectively, ethyl 2-acetyl-9-phenoxynonanoate [I; Ar is C$_6$H$_5$, Alk is (CH$_2$)$_7$, R is CH$_3$CO, R' is CH$_3$CH$_2$OCO]; ethyl 2-acetyl-9-(4-chlorophenoxy)nonanoate [I; Ar is 4-ClC$_6$H$_4$, Alk is (CH$_2$)$_7$, R is CH$_3$CO, R' is CH$_3$CH$_2$OCO]; ethyl 2-acetyl-9-(4-bromophenoxy)nonanoate [I; Ar is 4-BrC$_6$H$_4$, Alk is (CH$_2$)$_7$, R is CH$_3$CO, R' is CH$_3$CH$_2$OCO]; ethyl 2-acetyl-9-(2,4,6-trichlorophenoxy)nonanoate [I; Ar is 2,4,6-Cl$_3$C$_6$H$_2$, Alk is (CH$_2$)$_7$, R is CH$_3$CO, R' is CH$_3$CH$_2$OCO]; or ethyl 2-acetyl-5-(2-chloro-4-methoxyphenoxy)pentanoate [I; Ar is 2-Cl-4-CH$_3$-OC$_6$H$_3$, Alk is (CH$_2$)$_3$, R is CH$_3$CO, R' is CH$_3$CH$_2$OCO].

According to the procedures described hereinabove starting from the appropriate substitute phenol, alkylene dibromide and keto-ester, the following compounds were prepared:

EXAMPLE 2: Ethyl 2-acetyl-11-(2-chloro-4-methoxyphenoxy)undecanoate [I; Ar is 2-Cl-4-CH$_3$OC$_6$H$_3$, Alk is (CH$_2$)$_9$, R is CH$_3$CO, R' is CH$_3$CH$_2$OCO], golden yellow oil.

Anal. Calcd. for C$_{22}$H$_{33}$ClO$_5$: C, 63.99; H, 8.06; Cl, 8.59. Found: C, 64.55; H, 8.18; Cl, 8.91. 64.49 8.20

IR (oil film)$\nu_{(cm-1)}$: 3070vw, 2995sh, 2985sh (arom.), 2930s (—CH$_3$); 2850ms (—CH$_2$—); 1738s, 1720s (C=O); 1595s; 1270ms; 1210s; 1050ms+shldr.

NMR (20% CDCl$_3$; internal TMS) δ ppm (Ratio): 6.9(3) (arom.); 4.25 (2 of 8) (O—CH$_2$—CH$_3$); 3.98 (2 of 8) (—O—CH$_2$—CH$_2$—); 3.77 (3 of 8) (O—CH$_3$); 3.42 (1 of 8) (—CH—(C=O)$_2$); 2.22(3) (CH$_3$—C=O).

EXAMPLE 3: Ethyl 2-acetyl-6-(2-chloro-4-methoxyphenoxy)hexanoate [I; Ar is 2-Cl-4-CH$_3$OC$_6$H$_3$, Alk is (CH$_2$)$_4$, R is CH$_3$CO, R' is CH$_3$CH$_2$OCO], b.p. 190°–192° C. (0.12 mm.).

Anal. Calcd. for C$_{17}$H$_{23}$ClO$_5$: C, 59.56; H, 6.76; Cl, 10.34. Found: C, 59.71; H, 6.85; Cl, 10.28.

EXAMPLE 4: Ethyl 2-acetyl-7-(2-chloro-4-methoxyphenoxy)heptanoate [I; Ar is 2-Cl-4-CH$_3$OC$_6$H$_3$, Alk is (CH$_2$)$_5$, R is CH$_3$CO, R' is CH$_3$CH$_2$OCO], b.p. 198°–199° C. (0.13 mm.).

Anal. Calcd. for C$_{18}$H$_{25}$ClO$_5$: C, 60.59; H, 7.06; Cl, 9.94. Found: C, 60.58; H, 6.98; Cl, 10.05.

EXAMPLE 5: Ethyl 2-acetyl-12-(2-chloro-4-methoxyphenoxy)-dodecanoate [I; Ar is 2-Cl-4-CH$_3$OC$_6$H$_3$, Alk is (CH$_2$)$_{10}$, R is CH$_3$CO, R' is CH$_3$CH$_2$OCO], golden yellow oil.

Anal. Calcd. for C$_{23}$H$_{35}$ClO$_5$: C, 64.70; H, 8.26; Cl, 8.30. Found: C, 64.99; H, 8.39; Cl, 8.50.

IR (oil film )$\nu_{(cm-1)}$: 3060vw, 3000sh, 2985sh (arom.); 2920s (CH$_3$); 2850ms (—CH$_2$—); 1740ms, 1715 ms (C=O); 1495s; 1270ms, 1210ms; 1050ms+shldr.

Example 6: Ethyl 2-acetyl-8-(2-chloro-4-methoxyphenoxy)octanoate [I: Ar is 2-Cl-4-CH$_3$OC$_6$H$_3$, Alk is (CH$_2$)$_6$, R is CH$_3$CO, R' is CH$_3$CH$_2$OCO], light yellow oil.

Anal. Calcd. for C$_{19}$H$_{27}$ClO$_5$: C, 61.53; H, 7.34; Cl, 9.56. Found C, 61.31; H, 7.46; Cl, 9.79.

IR (oil film )$\nu_{(cm-1)}$: 3060vw, 3000sh, 2985sh (arom.); 2940ms (CH$_3$); 2860m (—CH$_2$—); 1740ms; 1720ms (C=O); 1495s; 1270ms; 1210ms; 1050ms+shldr.

NMR (20% CDCl$_3$; internal TMS) δppm (Ratio); 6.68-70(3) (arom.); 4.16 (2 of 8) (O—CH$_2$—CH$_3$); 3.92 (2 of 8) (—O—CH$_2$—CH$_2$—); 3.70 (3 of 8) (—OCH$_3$); 3.38 (1 of 8) (—CH—(CO—)$_2$); 2.16 (3) (—CO—CH$_3$); 1.22 (3 of 16) (—CH$_2$CH$_3$).

We claim:

1. A compound of the formula

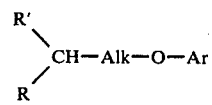

wherein:
Alk is alkylene of 3 to 10 carbon atoms;
R is alkanoyl of 2 to 6 carbon atoms;
R' is carboalkoxy of 2 to 6 carbon atoms;
and Ar is phenyl or phenyl substituted by one to three substituents selected from the group consisting of alkoxy of 1 to 4 carbon atoms and halogen.

2. Ethyl 2-acetyl-9-(2-chloro-4-methoxyphenoxy)-nonanoate, according to claim 1.

3. Ethyl 2-acetyl-11-(2-chloro-4-methoxyphenoxy)undecanoate, according to claim 1.

4. Ethyl 2-acetyl-6-(2-chloro-4-methoxyphenoxy)-hexanoate, according to claim 1.

5. Ethyl 2-acetyl-7-(2-chloro-4-methoxyphenoxy)-heptanoate, according to claim 1.

6. Ethyl 2-acetyl-12-(2-chloro-4-methoxyphenoxy)-dodecanoate, according to claim 1.

7. Ethyl 2-acetyl-8-(2-chloro-4-methoxyphenoxy)octanoate, according to claim 1.

8. A composition for combatting viruses which comprises an antivirally effective amount of at least one compound according to claim 1 in admixture with a suitable carrier or diluent.

9. A method for combatting viruses which comprises contacting the locus of said viruses with a composition containing an antivirally effective amount of at least one compound according to claim 1 in admixture with a suitable carrier or diluent.

* * * * *

UNITED STATES PATENT AND TRADEMARK OFFICE
CERTIFICATE OF CORRECTION

PATENT NO. : 4,171,376
DATED : October 16, 1979
INVENTOR(S) : Joseph C. Collins and Guy D. Diana It is certified that error appears in the above-identified patent and that said Letters Patent are hereby corrected as shown below:

Column 5, line 13, "formly" should read --formyl--;

line 21, "alkenoyl" should read -- -alkenoyl--.

Column 7, line 8, "$(Ch_2)_7$" should read --$(CH_2)_7$--;

line 68, "C, 64.55; H, 8.18; Cl, 8.91. 64.49 8.20" should read --C, 64.55; H, 8.18; Cl, 8.91.--
    64.49       8.20

Column 8, line 46, "$(-CH-(CO-_2)$" should read -- $(-CH-(CO-)_2)$ --.

Signed and Sealed this

Twenty-ninth Day of January 1980

[SEAL]

Attest:

SIDNEY A. DIAMOND

Attesting Officer

Commissioner of Patents and Trademarks